(12) United States Patent
Estrada (10) Patent No.: US 9,011,322 B2
(45) Date of Patent: Apr. 21, 2015

(54) LARYNGOSCOPE BLADE

(71) Applicant: Carlos Estrada, Brooklyn, MI (US)

(72) Inventor: Carlos Estrada, Brooklyn, MI (US)

( * ) Notice: Subject to any disclaimer, the term of this patent is extended or adjusted under 35 U.S.C. 154(b) by 227 days.

(21) Appl. No.: 13/660,401

(22) Filed: Oct. 25, 2012

(65) Prior Publication Data

US 2013/0109922 A1 May 2, 2013

Related U.S. Application Data

(60) Provisional application No. 61/553,625, filed on Oct. 31, 2011.

(51) Int. Cl.
*A61B 1/00* (2006.01)
*A61B 1/267* (2006.01)

(52) U.S. Cl.
CPC ............... *A61B 1/267* (2013.01); *A61B 1/0008* (2013.01)

(58) Field of Classification Search
USPC ................................................. 600/184–249
See application file for complete search history.

(56) References Cited

U.S. PATENT DOCUMENTS

| | | | |
|---|---|---|---|
| 1,568,732 A | 1/1926 | Haslinger | |
| 1,607,788 A | 11/1926 | Atkinson | |
| 4,112,933 A | 9/1978 | Moses | |
| 4,344,419 A * | 8/1982 | Burgin | 600/212 |
| 4,360,008 A * | 11/1982 | Corazzelli, Jr. | 600/194 |
| 4,384,570 A | 5/1983 | Roberts | |
| 4,573,451 A * | 3/1986 | Bauman | 600/190 |
| 4,793,327 A * | 12/1988 | Frankel | 600/194 |
| 4,827,910 A * | 5/1989 | Mathews, III | 600/194 |
| 4,832,020 A * | 5/1989 | Augustine | 128/207.14 |
| 4,947,829 A * | 8/1990 | Bullard | 600/101 |
| 5,203,320 A * | 4/1993 | Augustine | 600/187 |
| 5,381,787 A * | 1/1995 | Bullard | 600/188 |
| 5,498,231 A * | 3/1996 | Franicevic | 600/190 |
| 6,095,972 A * | 8/2000 | Sakamoto | 600/190 |
| 6,135,948 A * | 10/2000 | Lee | 600/189 |
| 6,251,069 B1 * | 6/2001 | Mentzelopoulos et al. | 600/196 |
| 6,602,188 B2 * | 8/2003 | Bolser | 600/210 |
| 7,153,260 B1 | 12/2006 | Girgis | |
| 7,695,433 B2 * | 4/2010 | Simons | 600/186 |
| 7,744,529 B2 | 6/2010 | Sakamoto | |
| 7,867,163 B2 * | 1/2011 | Chin et al. | 600/205 |
| 7,878,973 B2 * | 2/2011 | Yee et al. | 600/199 |
| 7,909,757 B2 * | 3/2011 | Herman | 600/190 |
| 7,955,256 B2 | 6/2011 | Sakamoto | |
| 8,074,655 B2 * | 12/2011 | Sanders | 128/848 |
| 8,317,693 B2 * | 11/2012 | Grey et al. | 600/212 |
| 8,337,402 B1 * | 12/2012 | Ellis | 600/199 |
| 2005/0234303 A1 * | 10/2005 | McMorrow | 600/189 |
| 2006/0074276 A1 * | 4/2006 | Cantrell | 600/196 |
| 2006/0247496 A1 | 11/2006 | Tjong Joe Wai | |

(Continued)

FOREIGN PATENT DOCUMENTS

FR 2821736 A1 9/2002

*Primary Examiner* — Mary Hoffman
*Assistant Examiner* — Michelle C Eckman
(74) *Attorney, Agent, or Firm* — Harness, Dickey & Pierce, P.L.C.

(57) ABSTRACT

A laryngoscope includes an elongated blade body having a proximal end and a distal end. The distal end of the blade body includes a plurality of arcuate slots therein. A movable tip extension is movably supported by the plurality of arcuate slots and movable in a forward and sideward direction beyond the distal end of the blade body. A guide member is attached to the movable tip extension for selectively moving the movable tip extension along the arcuate slots.

6 Claims, 8 Drawing Sheets

(56) References Cited

U.S. PATENT DOCUMENTS

| | | |
|---|---|---|
| 2008/0033249 A1* | 2/2008 | Sakamoto .................. 600/190 |
| 2008/0167530 A1* | 7/2008 | Minson ..................... 600/194 |
| 2009/0065000 A1* | 3/2009 | Chen ...................... 128/200.26 |
| 2010/0041955 A1* | 2/2010 | Grey et al. ................. 600/212 |
| 2010/0198017 A1* | 8/2010 | Raspallo ................... 600/190 |
| 2010/0261968 A1* | 10/2010 | Nearman et al. ............. 600/188 |
| 2011/0144436 A1* | 6/2011 | Nearman et al. ............. 600/188 |
| 2011/0319718 A1* | 12/2011 | Hakanen et al. ............. 600/193 |
| 2012/0022332 A1* | 1/2012 | De Domenico ............... 600/194 |
| 2012/0041268 A1* | 2/2012 | Grey et al. .................. 600/199 |
| 2012/0130176 A1* | 5/2012 | Minson ..................... 600/196 |

* cited by examiner

LARYNGOSCOPE BLADE

CROSS-REFERENCE TO RELATED APPLICATIONS

This application claims the benefit of U.S. Provisional Application No. 61/553,625, filed on Oct. 31, 2011, the disclosure of which is incorporated herein by reference.

FIELD

The present disclosure relates to a laryngoscope blade, and more particularly to a laryngoscope blade having a mechanism for moving an epiglottis of a patient to a side of the device.

BACKGROUND

This section provides background information related to the present disclosure which is not necessarily prior art.

A laryngoscope is a medical device that is used to position an endotracheal tube into a patient's trachea. In particular, a laryngoscope is used to expose a patient's larynx thereby allowing the insertion of an endotracheal tube past the patient's vocal cords and into the patient's trachea. The insertion of an endotracheal tube provides an airway for ventilation and prevents foreign substances from entering the patient's trachea and lungs.

SUMMARY

This section provides a general summary of the disclosure, and is not a comprehensive disclosure of its full scope or all of its features.

A laryngoscope includes an elongated blade body having a proximal end and a distal end. The distal end of the blade body includes a plurality of arcuate slots therein. A movable tip extension is movably supported by the plurality of arcuate slots and movable in a forward and sideward direction beyond the distal end of the blade body. A guide member is attached to the movable tip extension for selectively moving the movable tip extension along the arcuate slots. The laryngoscope is free from any pinch points. The location of the guide member and the movable tip are strategically designed to provide a pinch-free design to avoid contact with the patient's soft tissue of the pharynx.

According to a further aspect of the present disclosure, a laryngoscope includes an elongated blade body having a proximal end and a distal end. A movable tip extension is movably supported at the distal end of the blade body. Means are provided for guiding movement of the movable tip extension beyond the distal end of the blade body. A guide member is attached to the movable tip extension for moving the movable tip extension relative to the blade body.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

With reference to FIGS. 1-5 a laryngoscope blade 10 according to the principles of the present disclosure will now be described. The laryngoscope blade 10 includes a blade body 12. The blade body 12 can have a generally straight shape with a tip portion 14 having a curved shape, as best illustrated in the side view of FIG. 3. Alternatively, it should be understood that the blade body 12 could be curved and the tip portion 14 can be generally straight. The side of blade body 12 can be contoured to have a recessed side surface 15 to facilitate insertion in the patient's oral cavity and to provide greater clearance of the patient's right lower molars.

Figure 1:
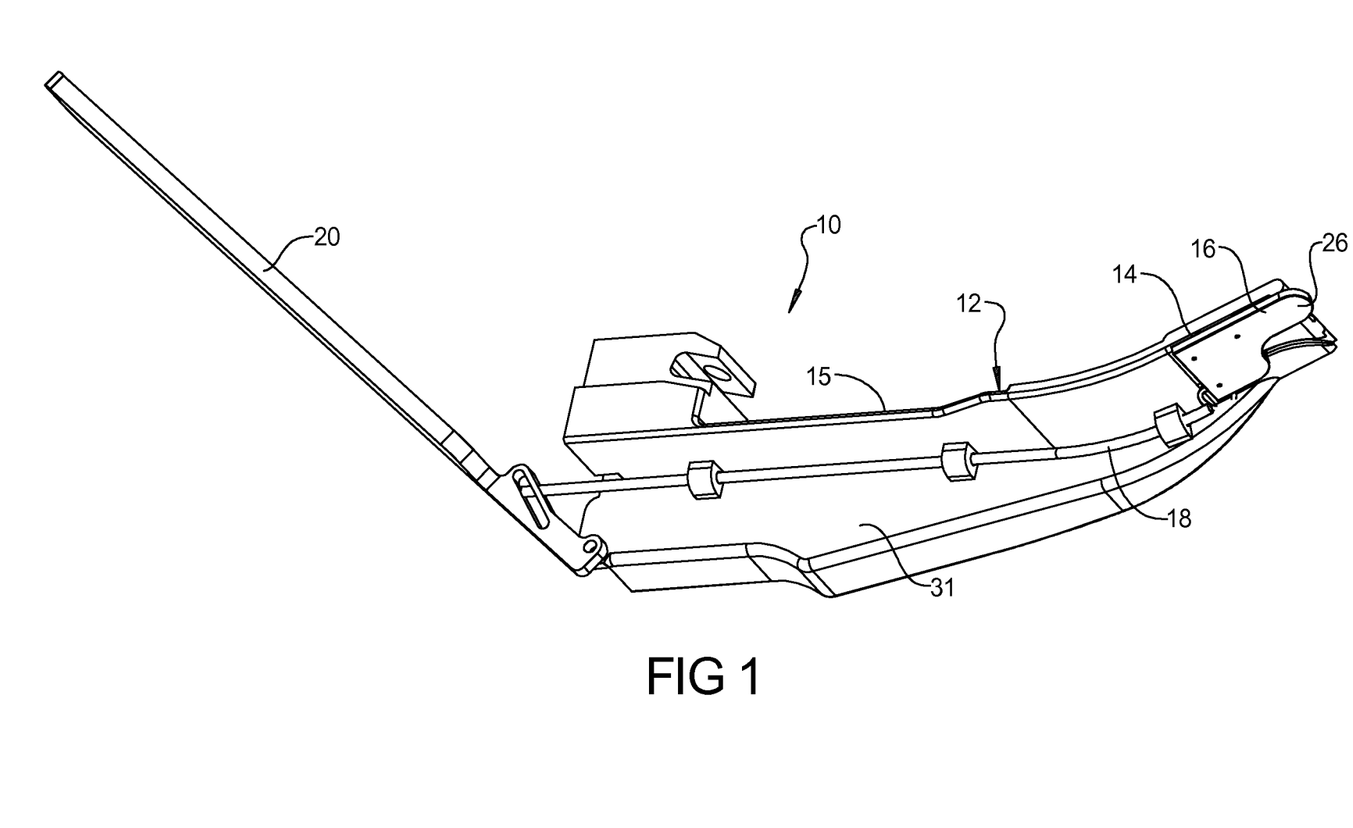
FIG. 1 is a perspective view of a laryngoscope blade according to the principles of the present disclosure.
Figure 2:
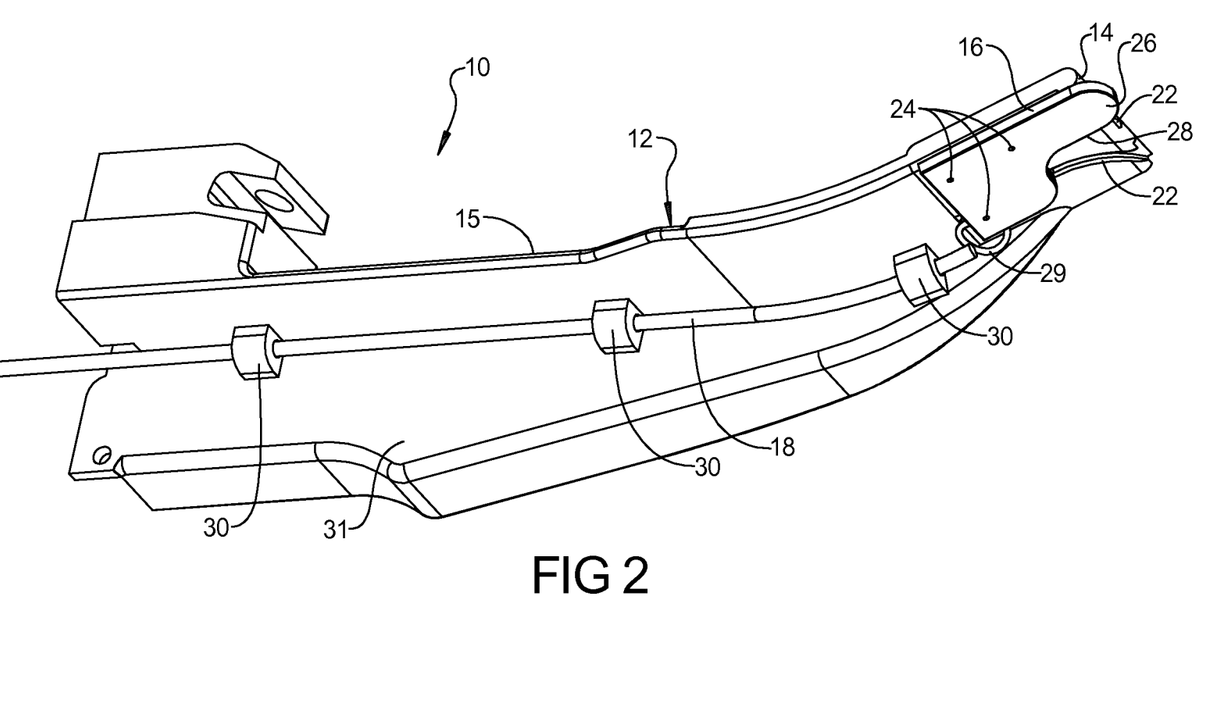
FIG. 2 is a close-up perspective view of the laryngoscope blade according to the principles of the present disclosure with the lever arm removed.
Figure 3:
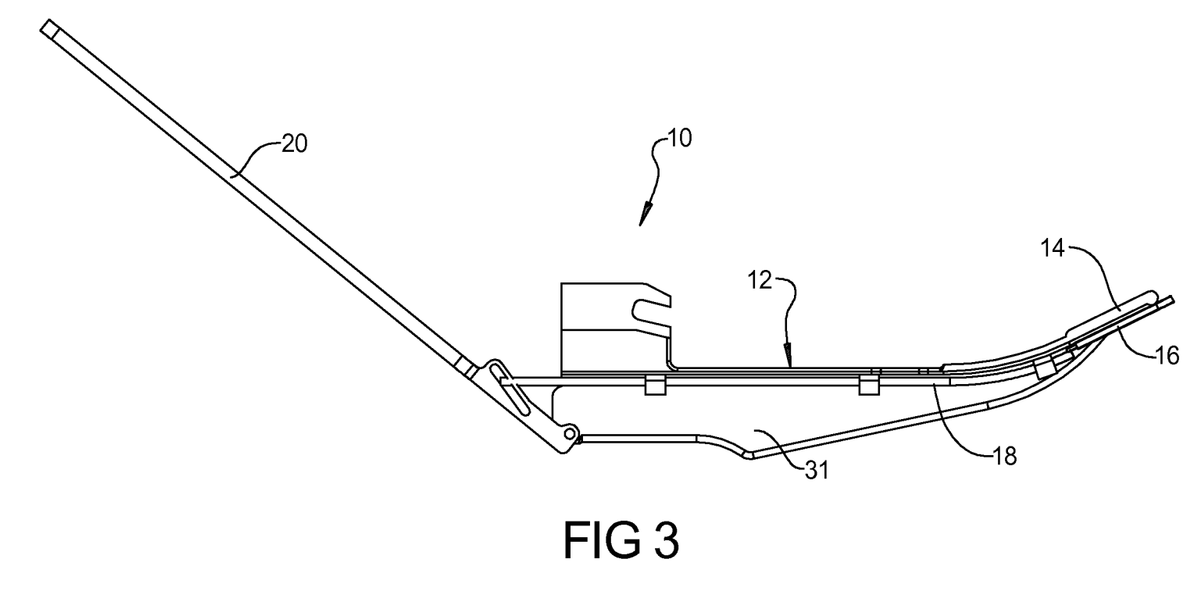
FIG. 3 is a side plan view of the laryngoscope blade shown in FIG. 1.
Figure 4:
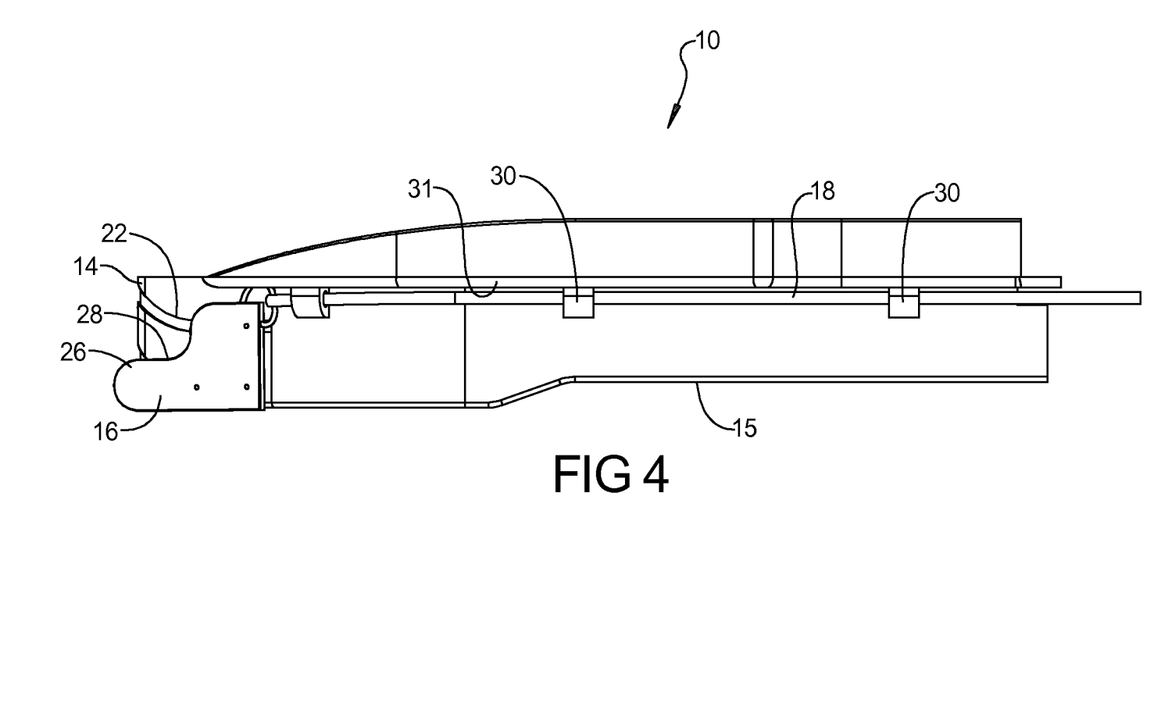
FIG. 4 is a bottom plan view of the laryngoscope blade shown in FIG. 1.
Figure 5:
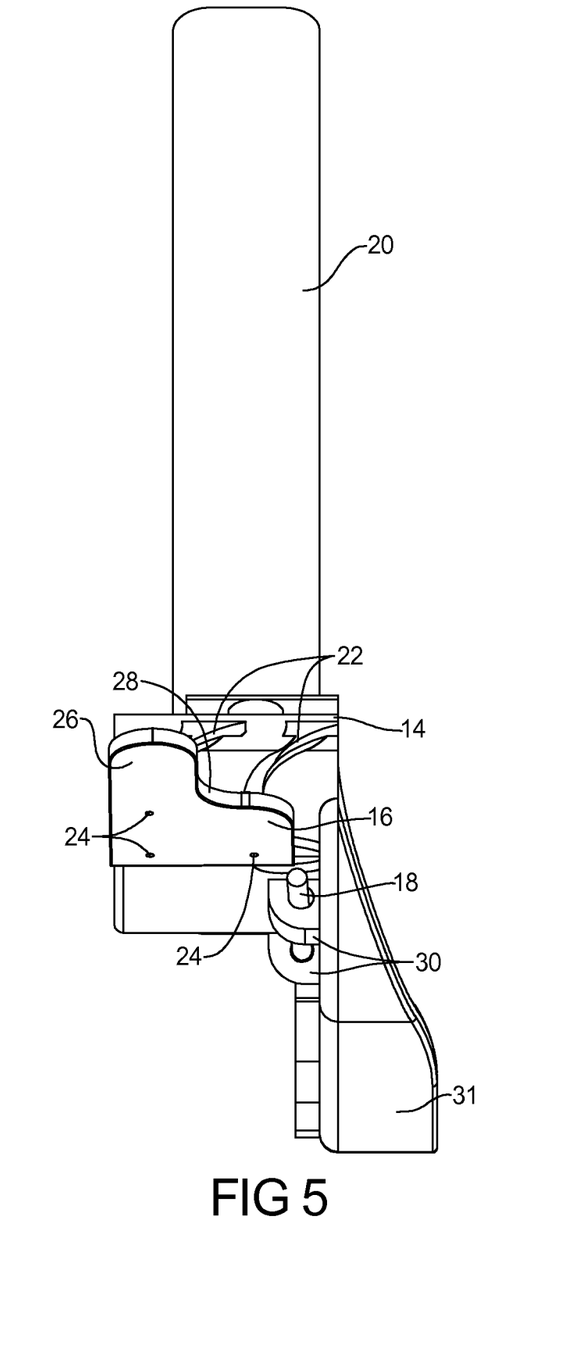
FIG. 5 is a front plan view of the laryngoscope blade shown in FIG. 1.

As shown in FIG. 1, the tip portion 14 of the blade 10 includes a movable tip extension 16 that is engaged by a flexible cable 18. The flexible cable 18 is moved by a lever 20 pivotally attached to a proximal end of the blade body 12. The movable tip extension 16 can be supported by a plurality of arcuate guide tracks 22 (best shown in FIGS. 2, 4 and 5) via guide pins 24 or another similar guide structure.

Figure 6:
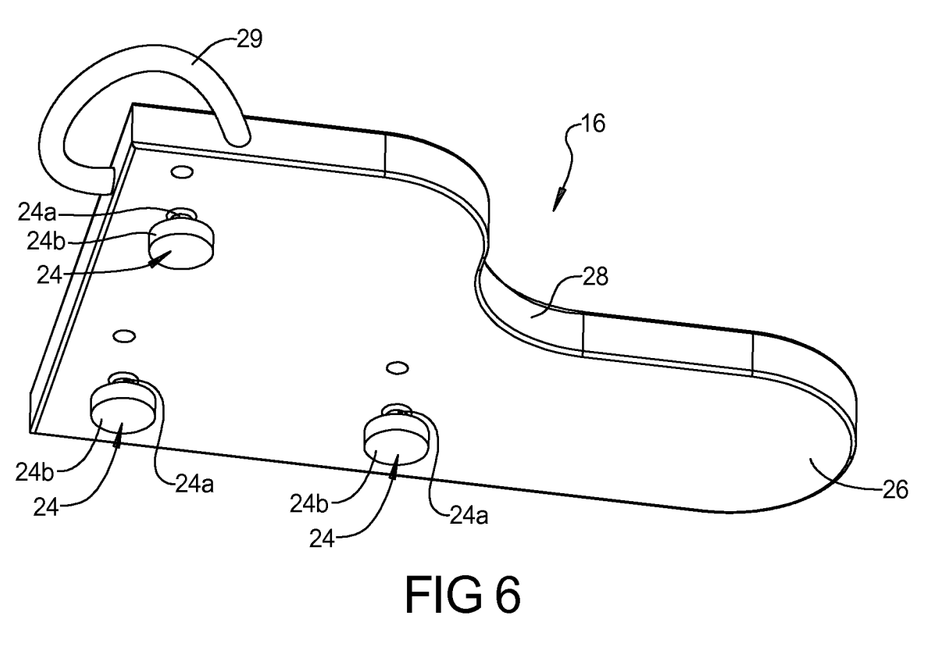
FIG. 6 is a perspective view of the movable tip extension shown in FIG. 1.

The lever 20 serves as an actuating device for moving the flexible cable 18 and thereby driving the movable tip extension 16 simultaneously in both a forward and sideward direction along the arcuate guide tracks 22 during insertion in the patient's throat. The tip portion 14 of the blade 10 can be brought adjacent to the patient's epiglottis, and operation of the lever 20 causes the cable 18 to push the movable tip extension 16 in an arcuate path along the arcuate guide tracks 22 so that a finger portion 26 of the movable tip extension 16 gently engages the epiglottis and moves it to one side of the patient's throat so as not to obstruct further insertion of the blade 10 and to allow unobstructed view of the trachea and insertion of an endotracheal tube. The finger portion 26 has a smooth arcuate side surface 28 that engages the epiglottis and gently pushes the epiglottis to one side as the movable tip extension is moved forward along the arcuate guide tracks 22. The arcuate guide tracks 22 can have a T-shaped cross-section (best shown in FIG. 5). As shown in FIG. 6, the guide pins 24 of the movable tip extension 16 can have a shank portion 24a and an enlarged head portion 24b. The tip extension 16 has an attachment portion 29 for attachment to the cable 18. The cable 18 is preferably flexible, yet rigid enough to allow the cable to push the tip extension 16. The cable 18 can be made from plastic or metal or other materials, and can be received in guide members or channels 30 provided on the blade body 12.

The location of the flexible cable 18, the lever 20, and the connection of the flexible cable 18 with the tip extension 16 are all strategically placed to avoid contact with the patient's soft tissue of the pharynx to provide a pinch-free design. In particular, the cable 18 and attachment of the cable 18 to the tip extension 16 are placed along an L-shaped channel between the blade body 12 and a reinforcing structure 31 on a back side of the blade body 12.

Further, it should be understood that the guide tracks 22 can have a straight shape that is parallel to or angled relative to the axial length of the blade body 12 and that the side surface 28 of the movable tip extension can have various shapes to effect a sideward movement of the epiglottis when the movable tip extension is moved axially along the guide tracks. Further, it should be understood that the guide tracks can be placed on the tip extension and the guide pins or other similar structure can be placed on the blade body. Further alternative mechanisms such as linkages can be used for guiding the movable tip extension along a desired path for moving the epiglottis in a sideward direction.

Figure 7:
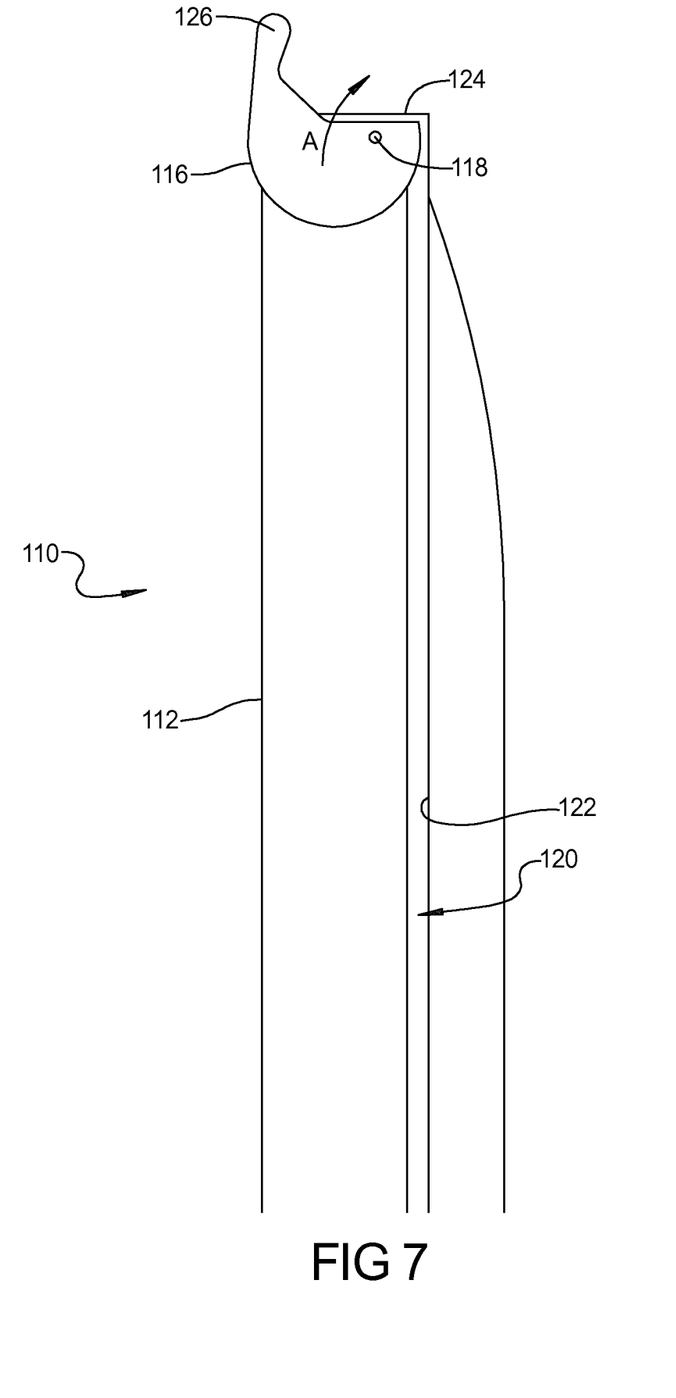
FIG. 7 is a bottom plan view of a second alternative laryngoscope blade.

As shown in FIG. 7, a laryngoscope blade 110 can include a blade body 112 and a pivoting tip extension 116 attached to the blade body 112 by a pivot pin 118. A pull cable 120 is attached to the tip extension 116 to cause pivoting movement of the tip extension 116 in the direction of arrow A. The pull cable 120 can be received in a guide channel 122 or guide loops. The pivoting movement of the tip extension 116 is in a laterally sideward direction relative to the generally planar tip 124 of the blade body. The tip extension 116 can include a protruding finger 126 that can engage the epiglottis and move it to a side when the tip extension 116 is pivoted.

Figure 8:
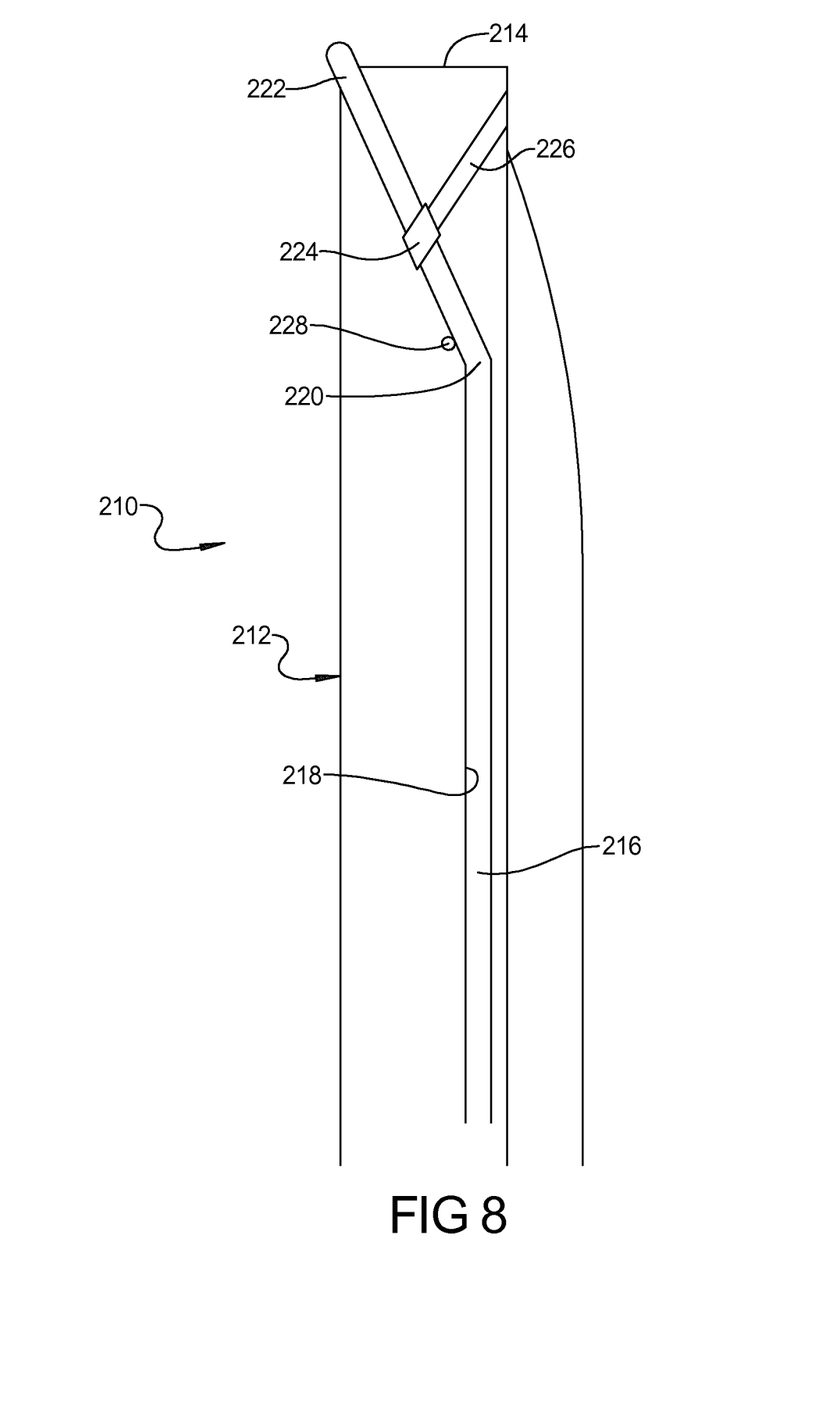
FIG. 8 is a bottom plan view of a third alternative laryngoscope blade.

According to an alternative embodiment, as shown in FIG. 8, a laryngoscope 210 includes a blade body 212 having a tip portion 214. A push/pull rod 216 is received in a retainer tube or guide loops 218 and can include a hinge point 220 and an extension portion 222. The extension portion 222 is engaged by a guide loop 224 that is slidably engaged with a guide track 226. Accordingly, as the rod 216 is pushed, the extension portion 222 pivots about the hinge point 220 and moves in a sweeping sideward motion as the guide loop 224 moves along the guide track 226 in a forward diagonal direction. A stopper pin 228 can be attached to the rod 216 and when it engages the guide loop 224 initiates the guide loop 224 sliding along the guide track 226 to initiate the sideward motion.

The use of an alternative driving mechanism other than the lever 20, such as a push button or other actuating device such as a hydraulic, pneumatic, or electro-mechanical actuator, can also be utilized.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A laryngoscope, comprising:
    an elongated blade body having a proximal end and a distal end, said distal end of said blade body having a width dimension wider than a thickness dimension with the width of the blade terminating in a pair of lateral side edges, said distal end of said blade body having a plurality of arcuate slots therein that curve toward one of said lateral side edges of said elongated body as the slots extend longitudinally along the elongated body;
    a movable tip extension movably supported by said plurality of arcuate slots and movable in a forward direction along the blade body and a laterally sideward direction relative to said lateral side edges of said blade body so as to move in the laterally sideward direction as the movable tip extension moves beyond said distal end of said blade body; and
    a guide member attached to said movable tip extension for moving said movable tip extension along said arcuate slots.

2. The laryngoscope according to claim 1, wherein said movable tip extension includes a finger portion having an arcuate side surface.

3. The laryngoscope according to claim 1, further comprising a lever attached to said guide member and pivotally attached to said proximal end of said blade body.

4. A laryngoscope, comprising:
    an elongated blade body having a proximal end and a distal end, said distal end of said blade body having a width dimension wider than a thickness dimension with the width of the blade terminating in a pair of lateral side edges;
    a movable tip extension movably supported at said distal end of said blade body;
    means for guiding movement of said movable tip extension beyond said distal end of said blade body in a forward direction along the elongated blade body and a laterally sideward direction relative to said lateral side edges of said blade body so as to move in the laterally sideward direction as the movable tip extension moves beyond said distal end of said blade body; and
    a guide member attached to said movable tip extension for moving said movable tip extension relative to said blade body.

5. The laryngoscope according to claim 4, further comprising a lever attached to said guide member and pivotally attached to said proximal end of said blade body.

6. A method of inserting an endotracheal tube into a patient's trachea, comprising:
    inserting said elongated blade body into a patient's throat until a tip of the blade body is brought adjacent to a patient's epiglottis;
    causing movement of said movable tip extension to engage the patient's epiglottis and move it mediolaterally to one side of the patient's throat to allow unobstructed view of the trachea; and
    inserting an endotracheal tube into the trachea.

* * * * *